(12) United States Patent
Kory

(10) Patent No.: US 8,608,022 B1
(45) Date of Patent: Dec. 17, 2013

(54) HOSPITAL ISOLATION GOWN DISPENSER

(76) Inventor: Pierre D. Kory, Chappaqua, NY (US)

( * ) Notice: Subject to any disclaimer, the term of this patent is extended or adjusted under 35 U.S.C. 154(b) by 384 days.

(21) Appl. No.: 12/788,479

(22) Filed: May 27, 2010

Related U.S. Application Data

(60) Provisional application No. 61/181,324, filed on May 27, 2009.

(51) Int. Cl.
*B65D 83/00* (2006.01)
*A41D 13/12* (2006.01)

(52) U.S. Cl.
USPC .............. 221/33; 221/1; 221/45; 221/208

(58) Field of Classification Search
USPC ............................................ 221/33
See application file for complete search history.

(56) References Cited

U.S. PATENT DOCUMENTS

| | | | | |
|---|---|---|---|---|
| 2,224,746 A * | 12/1940 | Richstein | ............ | 2/48 |
| 3,045,815 A | 7/1962 | Abildgaard | | |
| 3,094,323 A * | 6/1963 | Catania | ............ | 271/33 |
| 3,230,546 A * | 1/1966 | Sabee | ............ | 2/114 |
| 3,503,494 A * | 3/1970 | Blatz et al. | ............ | 206/499 |
| 3,735,865 A * | 5/1973 | Smith | ............ | 206/390 |
| 4,130,228 A * | 12/1978 | Perrin | ............ | 225/19 |
| 4,390,096 A * | 6/1983 | Goldenberg | ............ | 206/390 |
| 4,543,668 A * | 10/1985 | Franklin | ............ | 2/48 |
| 4,677,697 A * | 7/1987 | Hayes | ............ | 2/159 |
| 4,884,299 A * | 12/1989 | Rose | ............ | 206/390 |
| 5,501,376 A | 3/1996 | Roda-Balzarini | | |
| 5,740,552 A * | 4/1998 | Smith | ............ | 2/48 |
| 6,223,934 B1 | 5/2001 | Shoenfeld | | |
| 6,276,381 B1 * | 8/2001 | O'Brien | ............ | 135/87 |
| 6,330,856 B1 | 12/2001 | Fitzgerald et al. | | |
| 6,412,655 B1 | 7/2002 | Stuetzel et al. | | |
| 6,446,831 B1 * | 9/2002 | Smith et al. | ............ | 221/48 |
| 6,481,594 B1 * | 11/2002 | Yeh et al. | ............ | 221/63 |
| 7,093,304 B2 | 8/2006 | Griesbach, III | | |
| 7,296,765 B2 | 11/2007 | Rodrian | | |
| 7,474,938 B2 | 1/2009 | Poliner | | |
| 7,588,168 B2 | 9/2009 | Bagwell et al. | | |
| 7,665,811 B2 | 2/2010 | Johanning | | |
| 2002/0040912 A1 | 4/2002 | McHugh | | |
| 2004/0134924 A1 * | 7/2004 | Hansen et al. | ............ | 221/9 |
| 2006/0117456 A1 | 6/2006 | Griesbach, III | | |
| 2007/0284387 A1 | 12/2007 | Ellswood et al. | | |
| 2008/0008865 A1 | 1/2008 | Luu et al. | | |
| 2009/0206101 A1 | 8/2009 | Friesen et al. | | |
| 2010/0012674 A1 | 1/2010 | Brownlee | | |
| 2010/0012675 A1 | 1/2010 | Formon et al. | | |
| 2010/0089939 A1 | 4/2010 | Morris et al. | | |
| 2013/0105511 A1 | 5/2013 | Graneto, III | ............ | 221/303 |
| 2013/0106154 A1 * | 5/2013 | Buie et al. | ............ | 297/217.1 |

\* cited by examiner

*Primary Examiner* — Ramya Burgess
*Assistant Examiner* — Kelvin L Randall, Jr.
(74) *Attorney, Agent, or Firm* — Gardner Groff Greenwald & Villanueva, PC

(57) ABSTRACT

An automated dispenser device for medical items such as hospital isolation gowns and methods of dispensing the medical equipment using these dispensers are disclosed. The dispenser optionally includes a touch-less dispensing mechanism to reduce the potential for contamination. The invention also includes a hospital isolation gown adapted for use with the automated dispenser device and various arrays or assemblies of such gowns for bulk loading into the automated dispenser device.

3 Claims, 14 Drawing Sheets

HOSPITAL ISOLATION GOWN DISPENSER

CROSS-REFERENCE TO RELATED APPLICATION

This application claims the benefit of U.S. Provisional Patent Application Ser. No. 61/181,324, filed May 27, 2009, which is hereby incorporated herein by reference.

TECHNICAL FIELD

The present invention relates generally to the field of dispensing medical equipment, and more particularly to dispensing a hospital isolation gown, and optionally also dispensing booties, gloves, hepa-filters, head gear, and/or other protective garments or equipment.

BACKGROUND

Multi-drug resistant bacteria and viruses, or "superbugs", are causing serious concerns about safety and illness at hospitals worldwide. The resistance rates of common organisms to standard antibiotic regimens are rapidly increasing, causing risks to patient health and safety both within and outside hospitals. It is also causing treatment costs and the length of hospital stays to increase significantly. *Staphylococcus Aureus*, an organism which causes many common infections, is now classified as multi-drug resistant in more than 50% of cases in hospitals. According to the US Center for Disease Control, 1.7 million people per year are infected with "healthcare related infections" at hospitals in the US alone, and that 99,000 people per year die from these infections. This is an existential crisis for hospitals—the superbugs are prevalent in the one place where people are most vulnerable to their attack.

The fight against superbugs has been likened to an "arms race" that will be difficult, if not impossible to win with drugs alone. The superbugs evolve very quickly to become resistant to new drugs. Currently, two primary methods are used to prevent infection: development of new antibiotics and increased use of sanitary measures in hospitals.

However, the pharmaceutical companies have little economic incentive to develop antibiotics and antivirals because of the low profitability when compared to drugs that can be developed and administered repeatedly to patients with chronic health issues. As a result, the development of new antibiotic and antiviral drugs to combat superbugs, although a major issue, receives less attention from the drug companies than it should.

A main strategy in combating the spread of these infections is through increased use of sanitary measures. The measures used by healthcare workers (HCW) to protect their patients from contracting such an infection include hand washing, use of latex gloves, respiratory masks, barrier gowns and strict physical isolation of patients. "Contact precautions" (wearing both gloves and gowns while touching a patient) is one modality that is increasingly employed in the fight.

These hospital isolation gowns are paper barrier gowns worn by HCW's when they come into contact with patients who are suspected of having a multi-drug resistant infection. The gowns are one-size-fits-all and they come in plastic packages of 8-12 gowns. They are sometimes put into "dispensers", which are no more than metal boxes on a hospital room wall, or sometimes they are just left in the packaging on a table in or near the infected room.

HCW's often fail to be 100% compliant with the wearing of hospital isolation gowns, and even when they comply, the gowns are not necessarily effective. Many reasons contribute to this finding: the gowns are often difficult to locate as they are stored only in central areas of medical wards; the gowns are time-consuming and awkward to open, unfold, and enter into; even when they are used, they often fail to prevent contamination because they are stored in bundles on open tables allowing multiple HCW's to contaminate the gowns when handling the packaging. Finally, the opening of the gown prior to entering into the gown also allows for contamination of the outer surface of the gown by often contacting the hands and clothes of the wearer In addition to the basic non-compliance with contact precautions inherent in the current system, the method of donning hospital isolation gowns is time-consuming and causes delays in the increasingly busy day of the HCW. Because the hospital isolation gowns are often not near the rooms where they are supposed to be worn, HCW's often do not wear the gowns if they will not be touching the patient (a violation of contact precautions as the entire patient room is considered to be contaminated so any contact with items in the room allows for contamination of clothing). Overcoming these limitations is an important step in preventing the further rise of MDR infections.

It is to the provision of an apparatus and method for dispensing one or more hospital isolation gowns and/or other items meeting these and other needs that the present invention is primarily directed.

SUMMARY

Described herein are dispenser devices for medical equipment that includes hospital isolation gowns and methods of dispensing the medical equipment using these dispensers.

In one aspect, the invention relates to an apparatus comprising a dispenser device for medical equipment. For example, an automated dispensing apparatus for medical items includes an enclosure for storing a plurality of medical items; and a dispensing mechanism for sequentially removing one of the plurality of medical items from the enclosure and presenting them to a user, the dispensing mechanism allowing the user to access the medical item without contact between the dispensing apparatus and the user and without contaminating a clean portion of the medical item being dispensed.

In another aspect, the invention relates to a dispenser for hospital gowns, comprising a frame, a receiver for receiving at least one hospital gown to be dispensed, means for maintaining the sterility of the at least one hospital gown prior to dispensing, and means for dispensing the at least one hospital gown from the receiver to a user.

In another aspect, the invention relates to a method of dispensing a hospital gown including the steps of placing the hospital gown inside a dispenser device, wherein the inside of the dispenser device is substantially sterile; securing the dispenser device; and dispensing the hospital gown through a dispenser port of the device.

In another aspect, the invention relates to a hospital gown or an array of hospital gowns adapted for dispensing from an apparatus as described herein.

In another aspect, the gown is dispensed in such a way to allow entry into a gown without touching the gown (i.e. "effortless entry" or "touchless entry"). In this aspect, no exterior (or any) handling of gown is needed prior to entering the gown.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

Figure 1A:
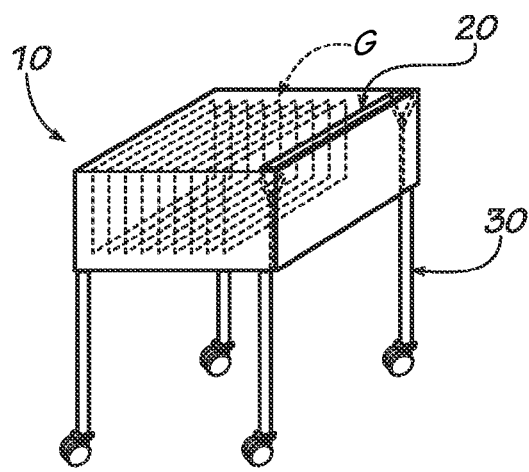
FIG. 1(a) shows a portable dispenser containing or storing medical equipment.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Described herein are dispenser devices and methods of using thereof. In this aspect, the dispenser devices dispense medical equipment that includes, but is not limited to, a hospital isolation gown, booties, gloves, hepa-filters, head gear, or any combination thereof. The medical equipment is packaged in such a way to readily allow dispensing by the dipensers described herein. For example, one-size-fits-all hospital isolation gowns may be packaged in a roll, similar to paper towels. In this aspect, 8-12 gowns may be packaged in the roll. The roll of hospital isolation gowns may then be placed into the dispenser and the dispenser is subsequently closed, creating a seal and barrier against potential outside contamination.

In certain aspects, the dispenser device is either an electronic dispenser or a manual dispenser that dispenses the medical equipment in a safe and sanitary manner and reduces the likelihood of multi-drug resistant infection. In one aspect, a person may push a button or wave their hand in front of a motion sensor and the medical equipment is subsequently dispensed via an electronic dispenser. The medical equipment can include a hospital isolation gown. In certain aspects, if the dispenser dispenses a hospital isolation gown, the gown may be dispensed by rolling the gown through an opening with a rubber-like valve or gasket that allows the gown to be dispensed but does not allow for the internal contents (i.e. the additional medical equipment or the additional isolation gowns) to become contaminated. In this aspect, sterility or substantial sterility may be maintained for the additional equipment that has not been dispensed.

In each of these aspects, the dispenser device can be a portable device readily transported from one destination to another or the dispenser device can be a fixed unit attached to a wall or to the floor. The dispenser device can be kept inside a hospital patient's room, immediately outside a patient's room, in an emergency room, an intensive care unit, medical wards, procedure rooms, imaging, suites, chemotherapy suites, anywhere that sterility is desired, or anywhere that a reduction in possible multi-drug resistant infection is desired when having contact with a patient.

Figure 1B:
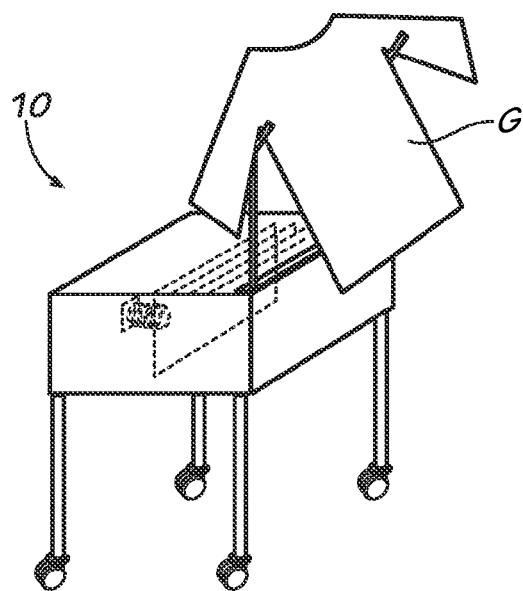
FIG. 1(b) shows the portable dispenser dispensing the medical equipment, where the medical equipment is a hospital isolation gown.
Figure 1C:
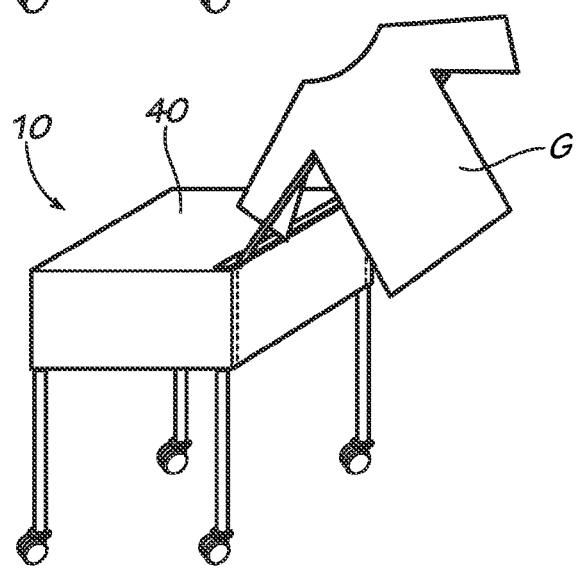
FIG. 1(c) shows the portable dispenser presenting the hospital isolation gown via extender rods for "effortless" or "touchless" entry.

In yet another aspect, the gown is dispensed in such a way to allow entry into gown without touching the gown (i.e. "effortless entry" or "touchless entry"). In this aspect, no exterior (or any) handling of gown is needed prior to entering the gown With reference now to the drawing figures, wherein like reference numbers represent corresponding parts throughout the several views, FIG. 1(a) shows a portable dispenser 10 with hospital isolation gowns G stored inside. FIG. 1(b) shows a single hospital isolation gown G being dispensed from the dispenser. In this figure, a spring is pushing the gown(s) towards the exit slot or receiver 20. FIG. 1(c) shows the device dispensing hospital isolation gown and allowing for "effortless" or "touchless" entry.

Figure 2A:
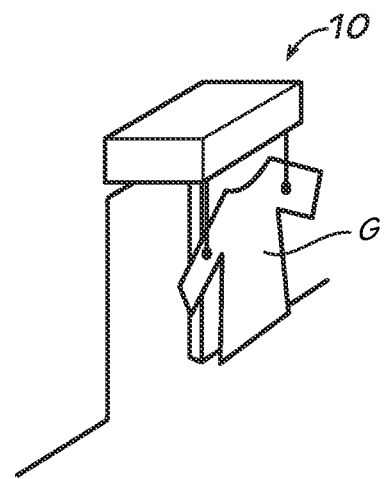
FIG. 2(a) shows a dispenser affixed to a wall above a door frame to a hospital room.
Figure 2B:
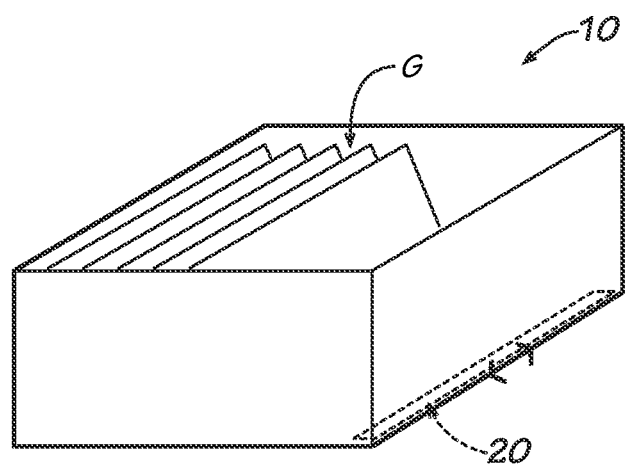
FIG. 2(b) shows a fixed dispenser containing or storing a hospital isolation gown.
Figure 2C:
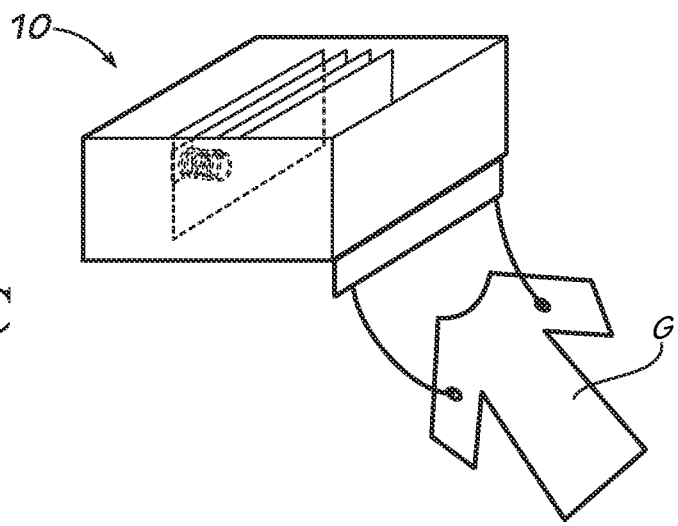
FIG. 2(c) shows the fixed dispenser dispensing the hospital isolation gown and allowing for "effortless" or "touchless" entry.

FIG. 2(a) shows a dispenser affixed to a wall above a door in a hospital room. FIG. 2(b) shows hospital isolation gowns G stored inside the dispenser, which can be permanently affixed to a wall. FIG. 2(c) shows the fixed dispenser dispensing the hospital isolation gown and allowing for "effortless" or "touchless" entry.

Figure 3A:
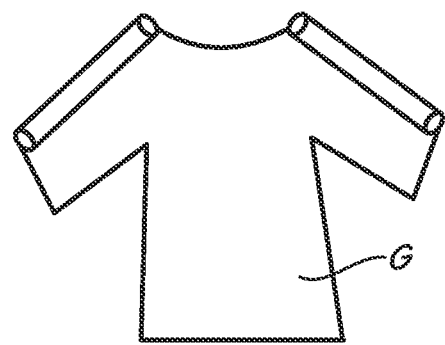
FIG. 3 shows an additional embodiment of the dispenser.
Figure 3B:
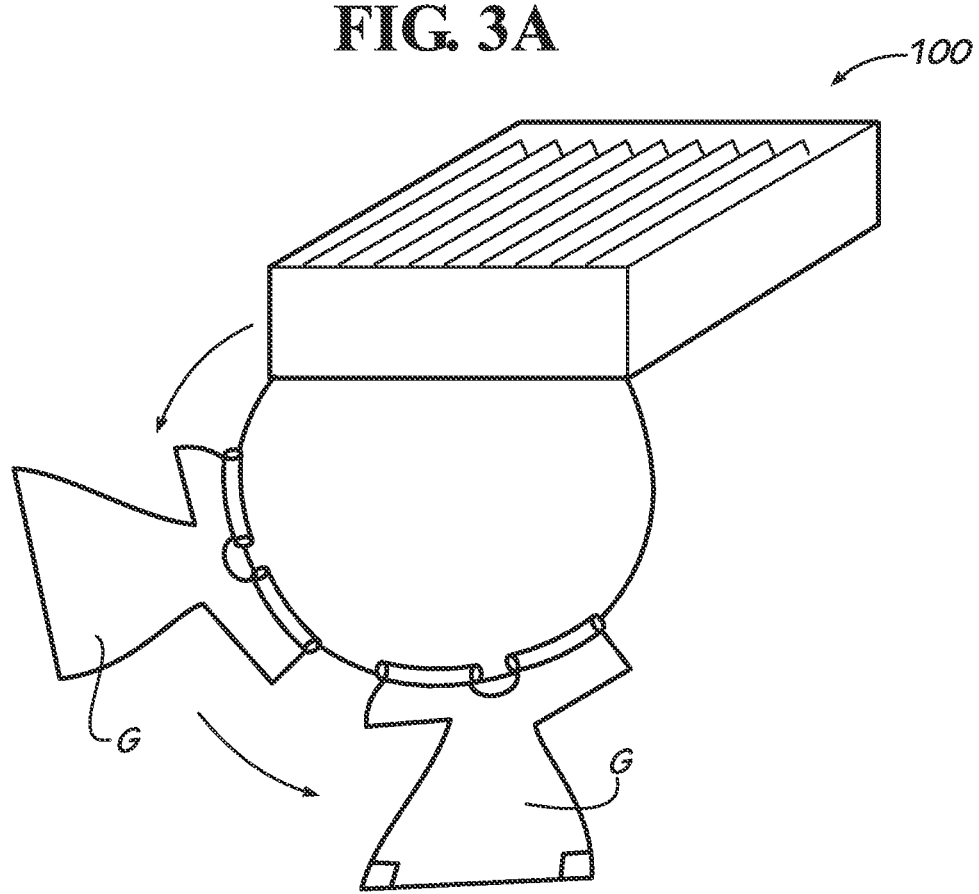

FIG. 3 shows an additional embodiment of the dispenser 100. The dispenser 100 shown in FIG. 3 can be modified to be a portable dispenser as shown in FIGS. 1(a)-1(c), or the dispenser shown in FIG. 3 can be modified to be affixed to an immobile object such as a wall as shown in FIGS. 2(a)-2(c).

Figure 4:
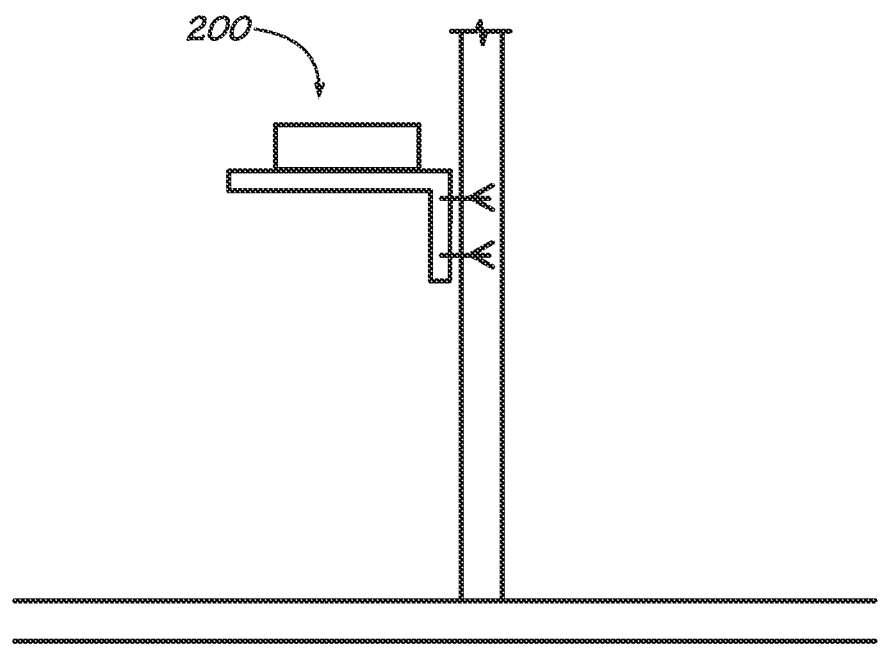
FIG. 4 shows a mounting option for a dispenser.
Figure 5A:
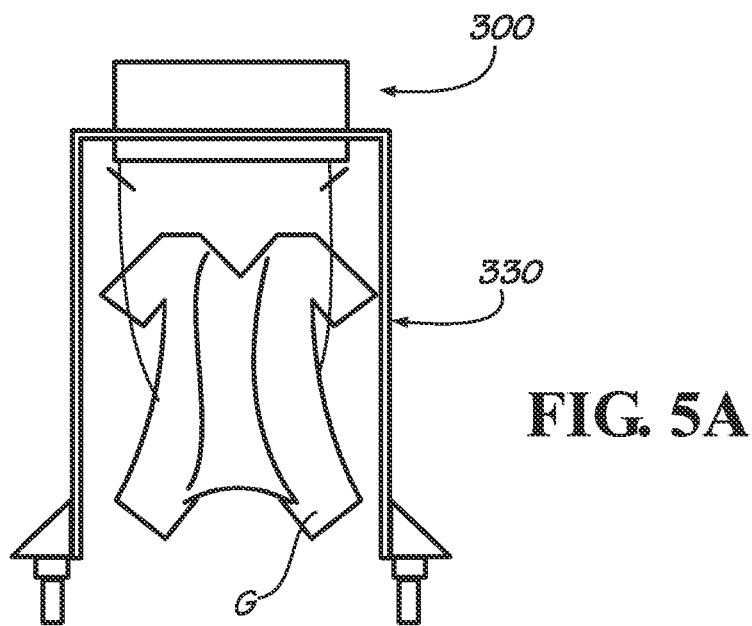
FIG. 5 shows a rolling dispenser embodiment.
Figure 5B:
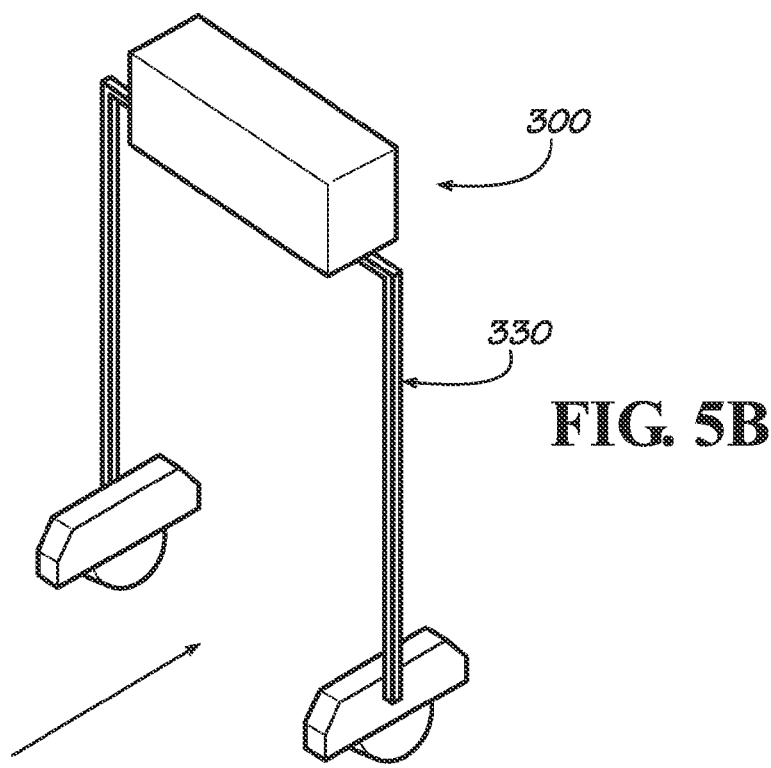

FIG. 4 shows an alternate mounting arrangement for a dispenser 200, according to another embodiment. FIG. 5 shows another embodiment, wherein the dispenser 300 is mounted to a frame 330 that has one or more wheels or casters for selectively repositioning the apparatus.

Figure 6:
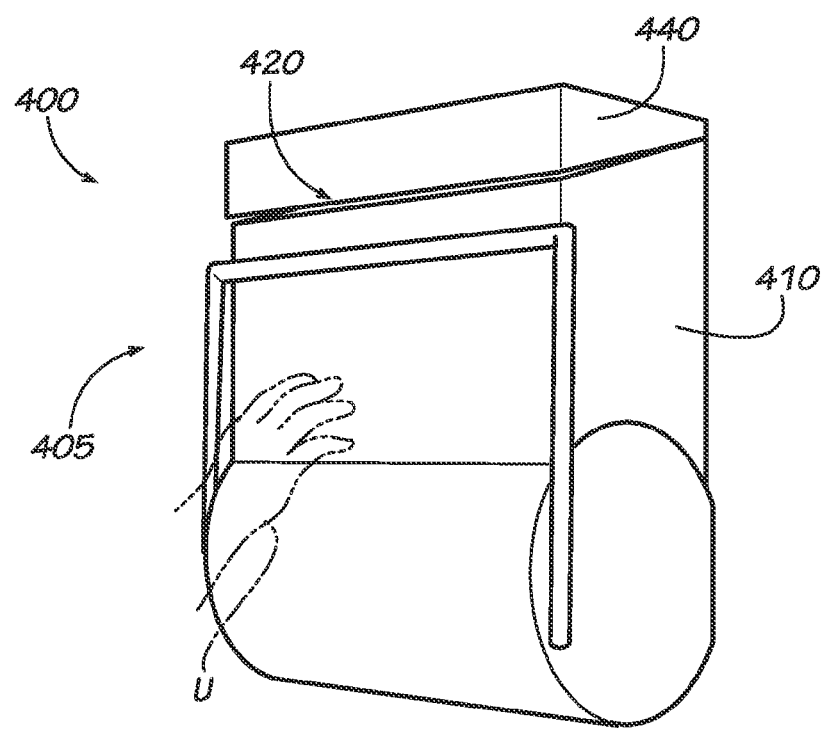
FIGS. 6-15 show a sequence of operation of a gown dispenser according to an example embodiment.

FIGS. 6-15 show a sequence of operation of an automated gown dispenser 400 according to another example form of the invention. In FIG. 6, a gown dispenser mechanism 405 includes a box shaped device or enclosure 410 enclosing a roll of barrier gowns G. Barrier gowns are designed for use in hospitals where health care workers clothes need protection from exposure to infectious or drug-resistant organisms while also preventing the contamination and spread of the organisms to a susceptible patient from the already contaminated or soiled clothing of the health care worker. The device allows for storage of gowns and has a lid 440 that allows for the gown G to be dispensed to wearer U as described below. The invention includes multiple attachment options of the dispenser—the dispenser can be installed on a wall or pole attached to a cart, with height adjustable and set so as to allow gown to be dispensed at an average shoulder height for ease of entry into sleeves, for example, approximately 5' off the ground. An optical sensor preferably located in center of the dispenser is triggered by hand movement, thus triggering the motor, which rotates the internal cylinder on which a roll of gowns G is seated.

Figure 7:
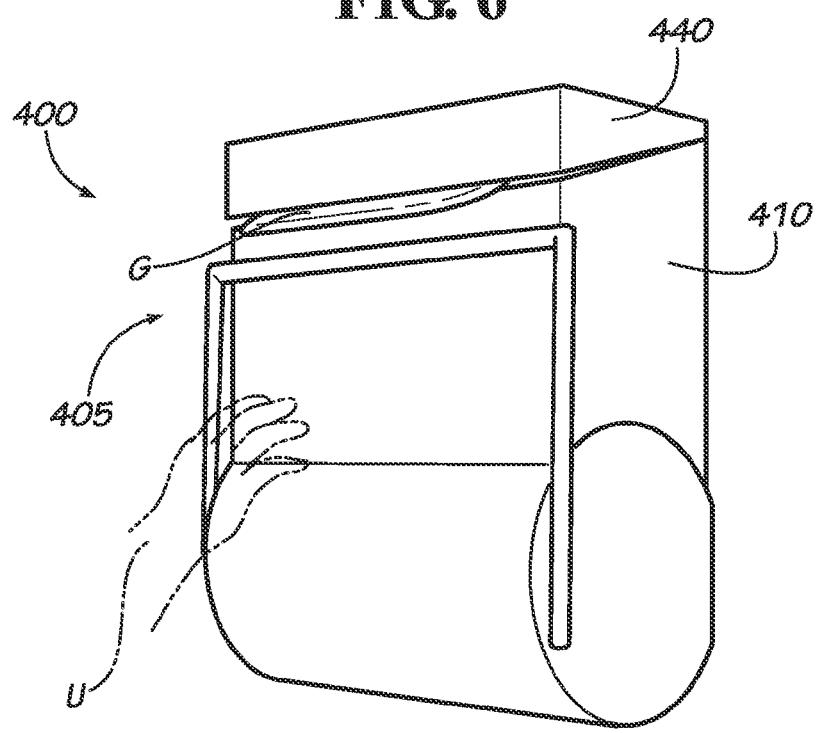
Figure 8:
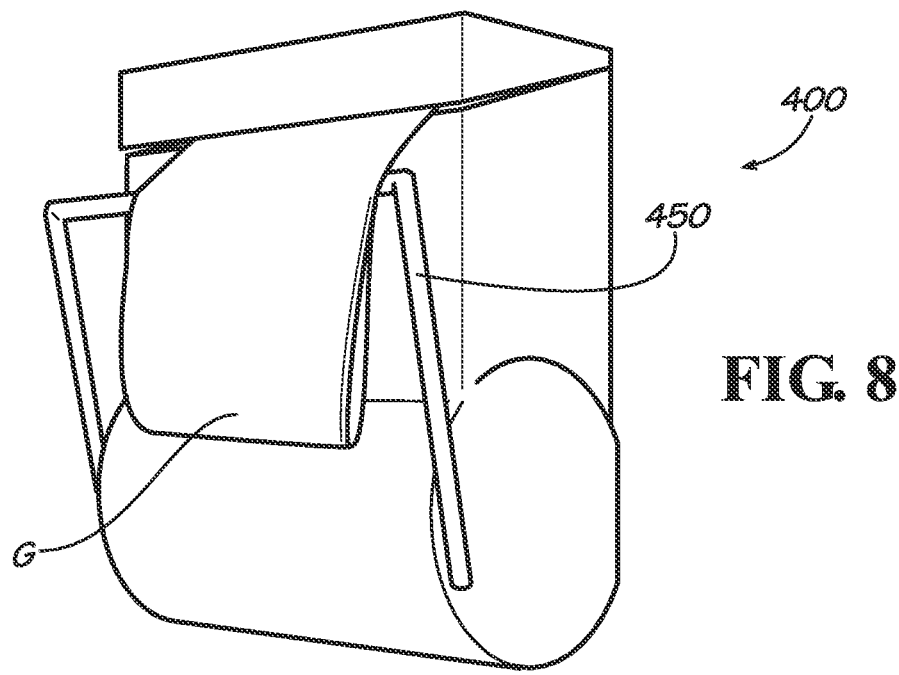

In FIG. 7, the top lid 440, which is normally closed, thus protecting the gowns from contamination or handling, is pushed open a short distance to allow the exit of the folded gown. An exit ramp portion of the dispenser is sloped so as to allow for downward descent of the gown toward wearer by force of gravity as well as pushing force of the roll and motor. In FIG. 8, the motor continues to turn, allowing for the gown to progress in exiting the device. As more of the gown G exits the holding chamber, a fixed arm 450 descends with it so as to push the gown G away from device and toward the wearer U, creating a space for entry of arms into sleeves of the gown by the wearer without the need to make any body position changes to avoid any physical obstructions or barriers to entry such as walls or other fixed objects.

Figure 9:
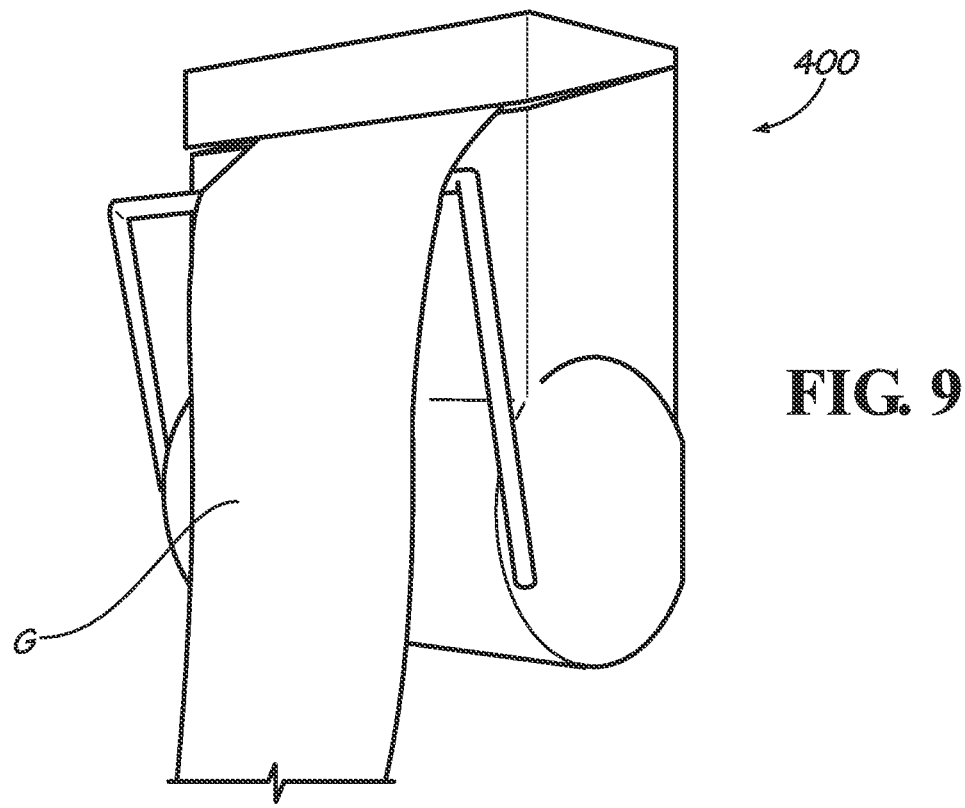
Figure 10:
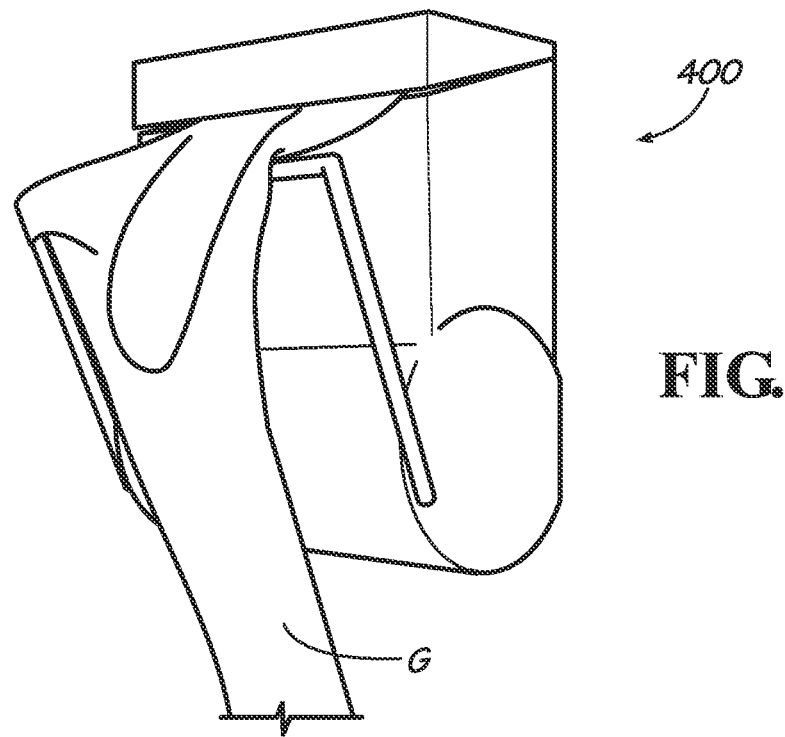
Figure 11:
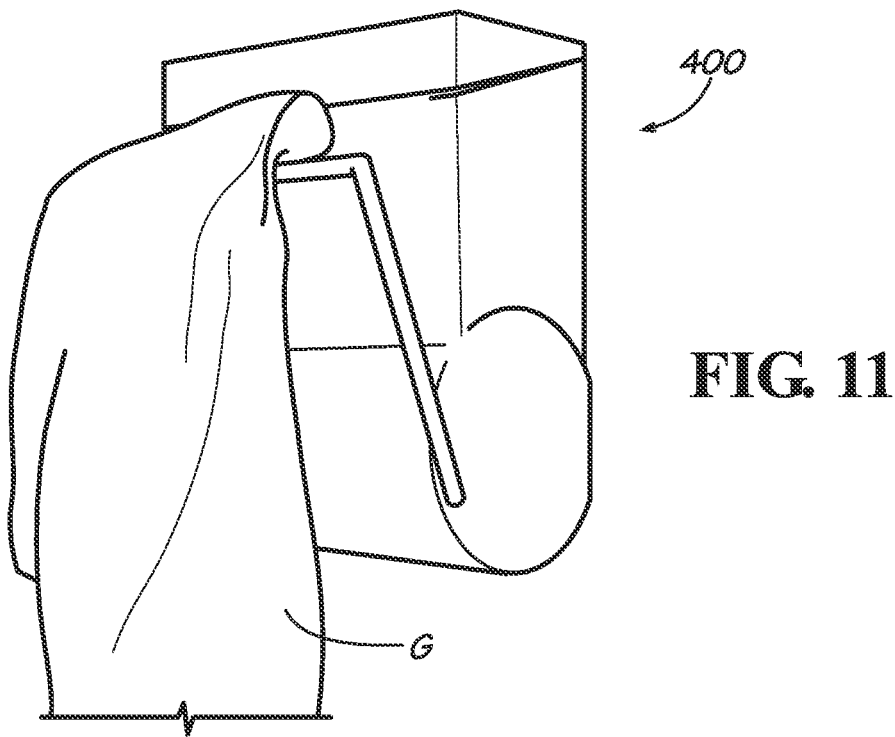
Figure 12:
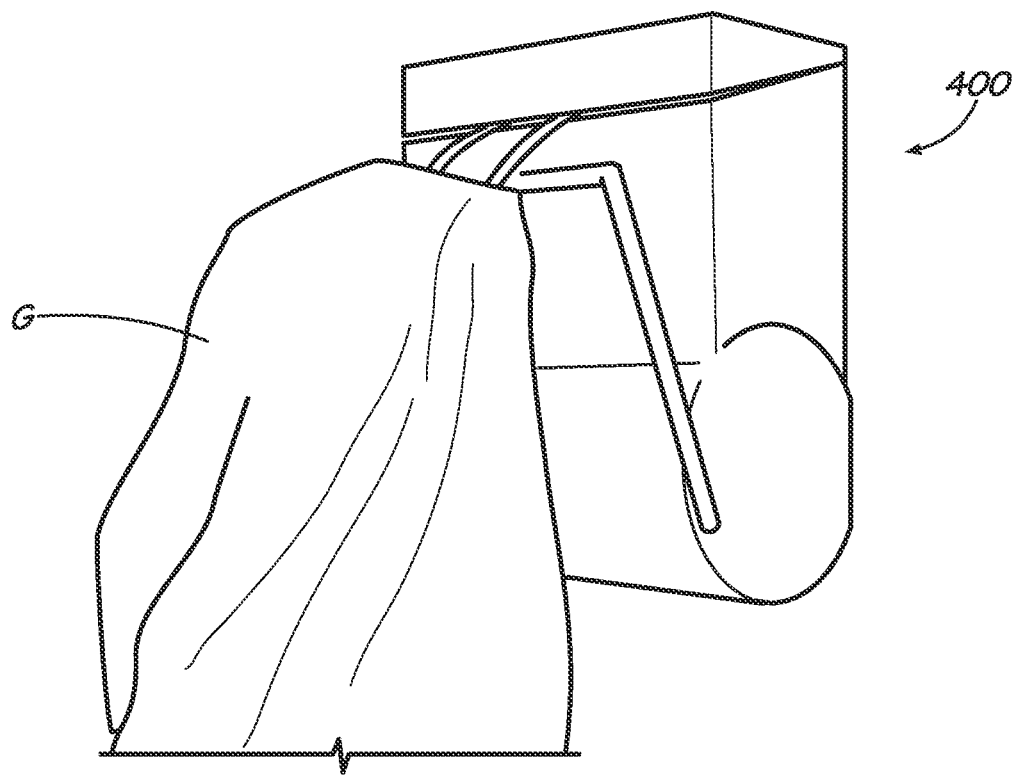

In FIG. 9, the fold of the exiting gown G is shown. The fold occurs down the center of the gown in a longitudinal orientation. The crease is approximately in the center of the folded gown, thus bringing the right and left sleeves to rest atop one another. In FIG. 10, the sleeves now begin to separate as the gown G further descends; this separation follows from how the gown was folded. FIG. 11 demonstrates further separation of the gown sleeves on the descent and exit of the gown. Shoulders of the gown are now at a height above ground approximating average shoulder height (4'-5' from floor). As shown in FIG. 12, two plastic tethers, attached between the collar of the exiting gown and the bottom hem of the following gown on the roll now appear. Exit of the gown is stopped by a set, programmed turning distance of the roll and motor.

Figure 13:
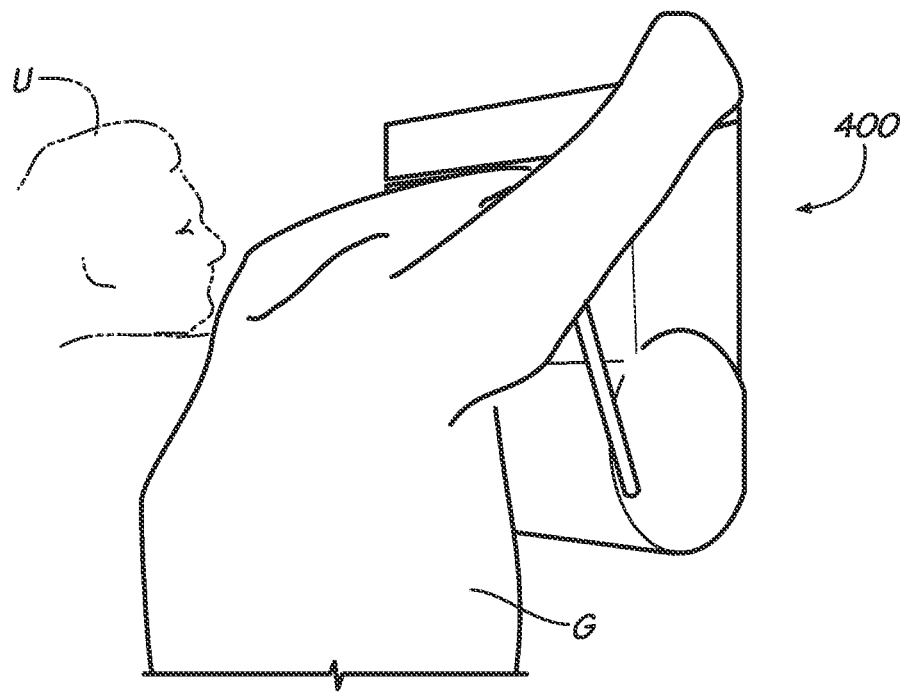
Figure 14:
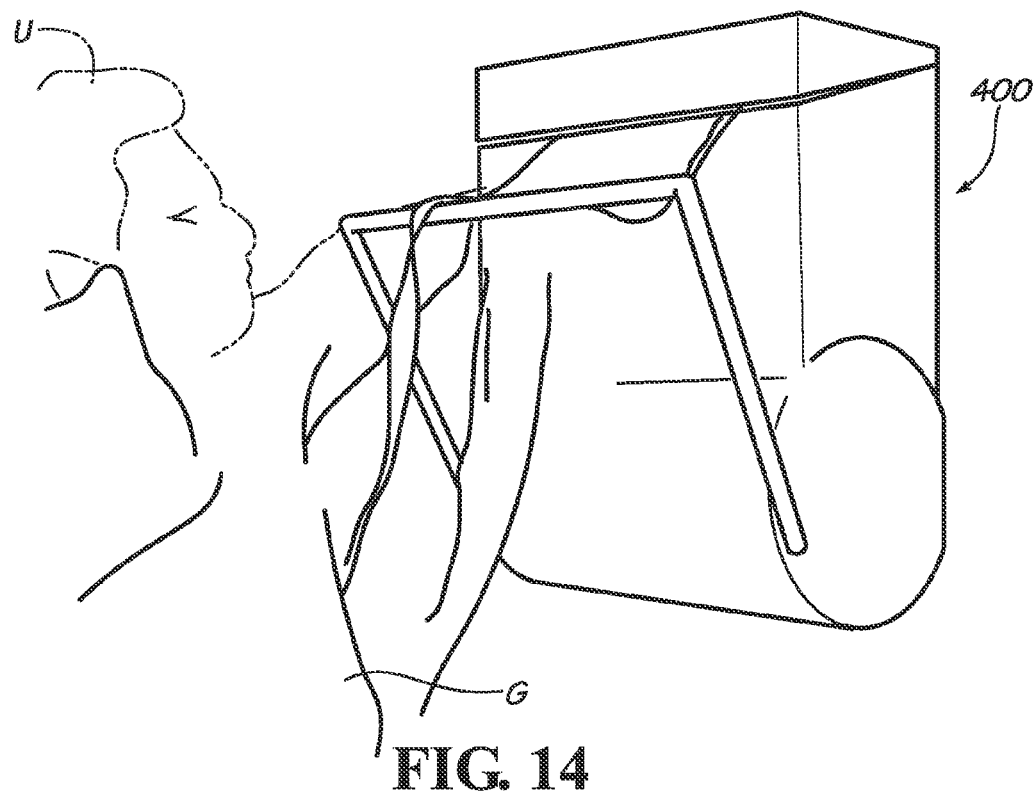
Figure 15:
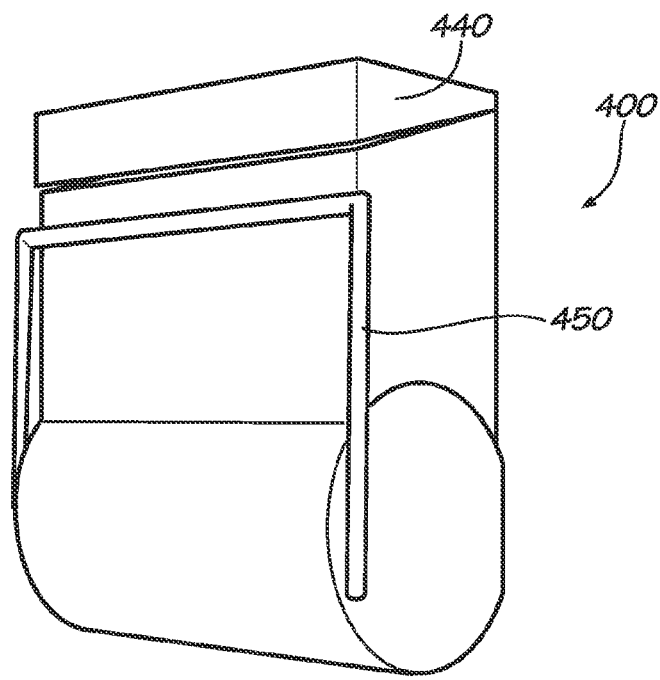

As shown in FIG. 13, the wearer U can now enter the gown without touching any of the gown exterior or the dispenser, only coming into contact with gown interior while placing their arms inside of the open, suspended sleeves of the gown. This prevents any contamination of gown exterior with soiled patient clothes. With reference then to FIG. 14, the arm enters the second sleeve, the wearer U now moves away from the device with their arms and/or body, creating a force which then tears apart the attachment tether between the wearers' gown and the following one on the roll. In FIG. 15, the pulling force created during the separation of the tether attachments between gowns triggers the gown presenting arm 450 to rotate back into place flush against the device and for the lid 440 to close, thus protecting the remaining gowns from exposure or contamination.

Figure 16:
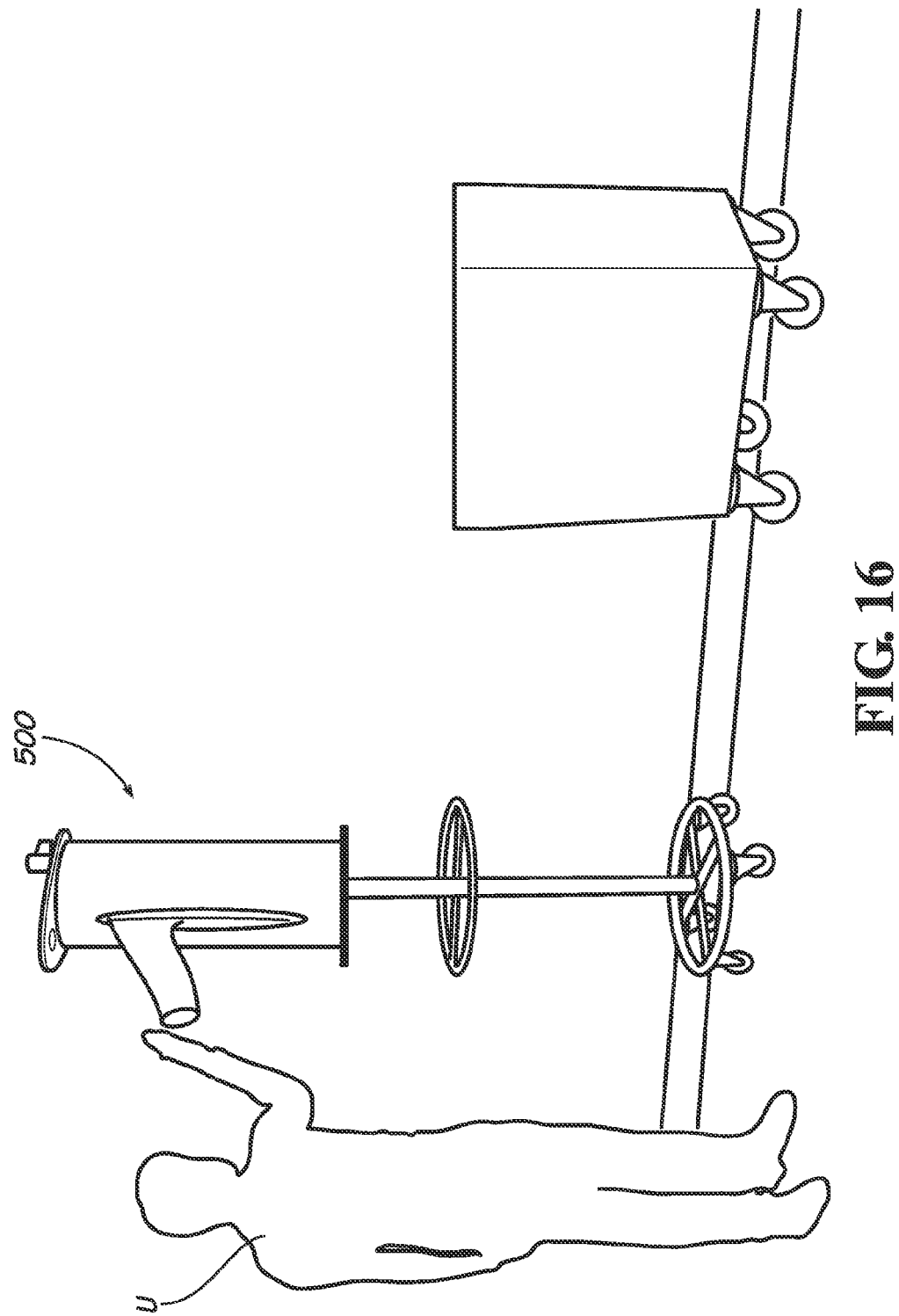
FIG. 16 shows a gown dispenser according to another example embodiment.
Figure 17:
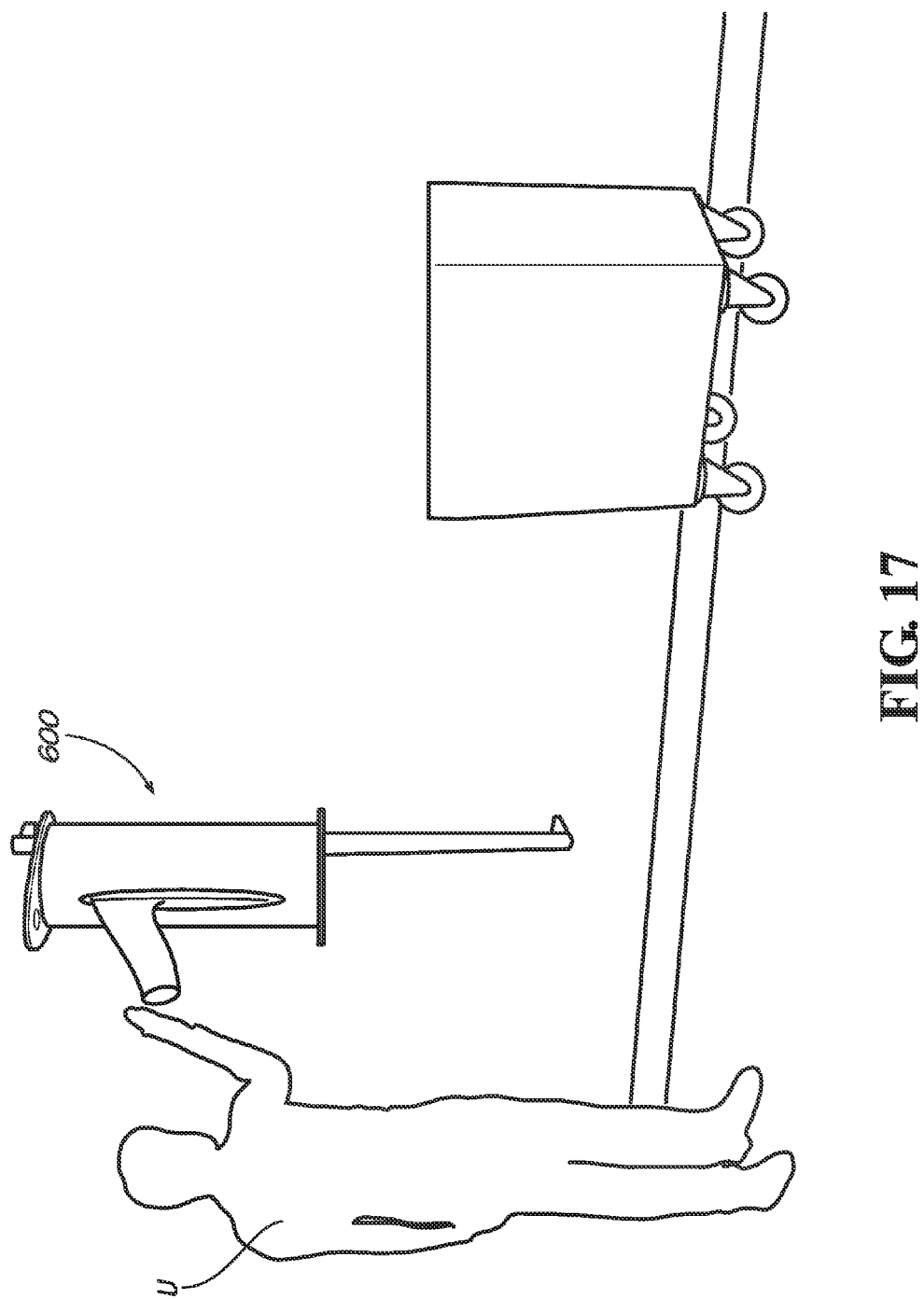
FIG. 17 shows a gown dispenser according to another example embodiment.
Figure 18:
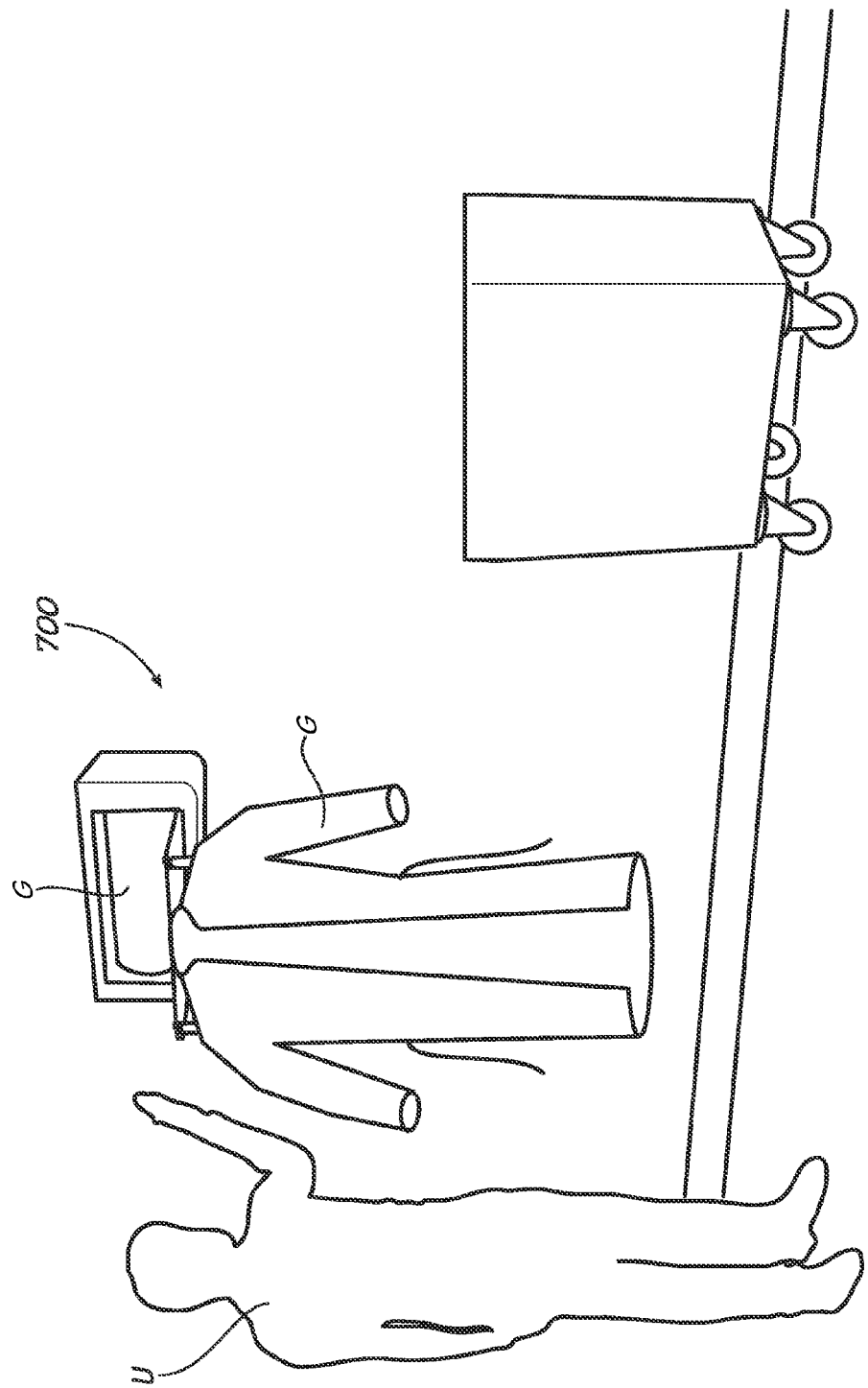
FIG. 18 shows a gown dispenser according to another example embodiment.
Figure 19:
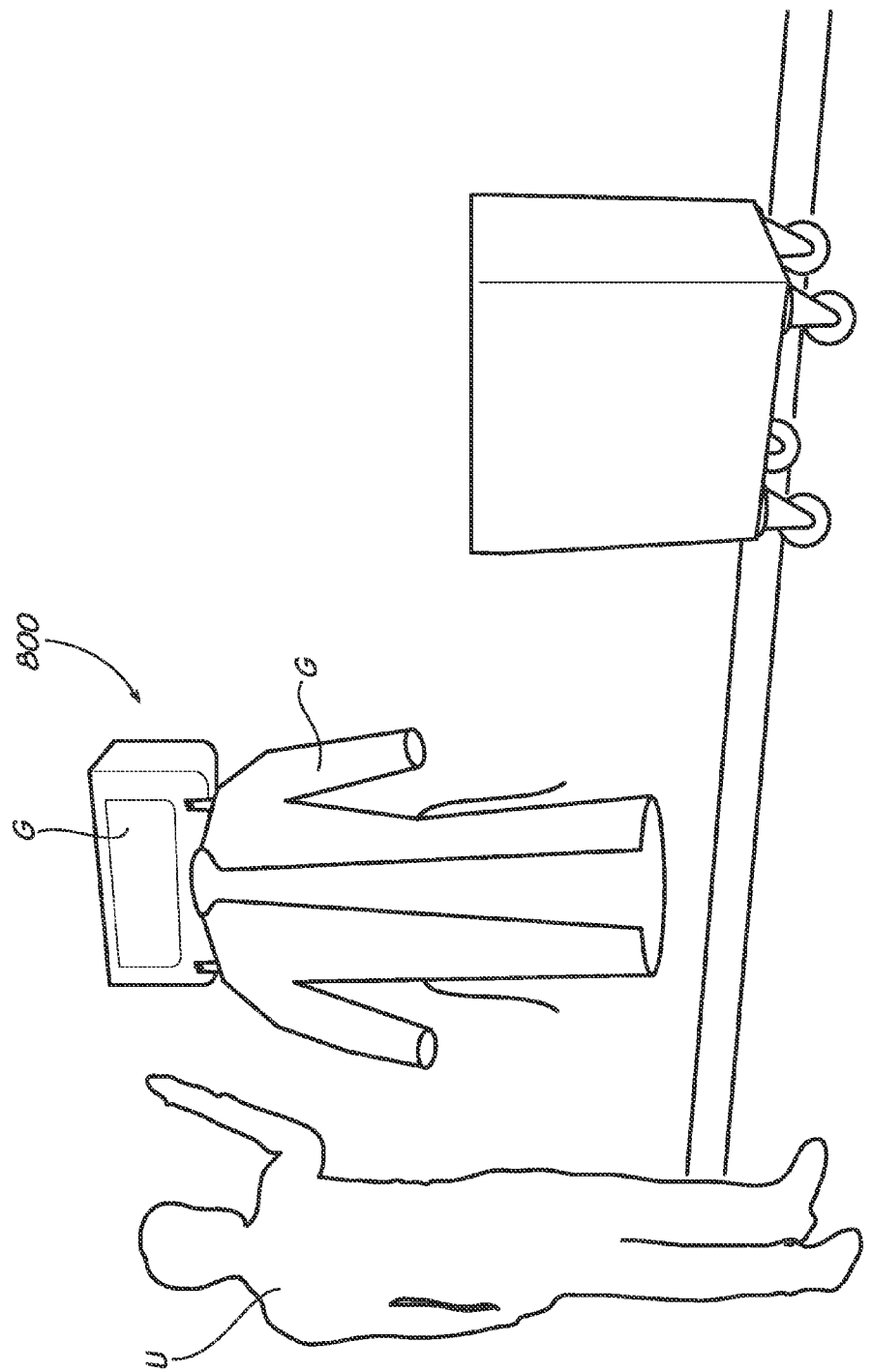
FIG. 19 shows a gown dispenser according to another example embodiment.

FIGS. 16-19 show various alternate forms of the invention. FIG. 16 is a vertical dispensing unit 500 mounted on a wheeled carriage for portability. FIG. 17 is a wall-mounted vertical dispensing unit 600. FIG. 18 is a wall-mounted horizontal dispensing unit 700 dispensing from a roll-fed array of gowns G. FIG. 19 is a wall-mounted horizontal dispensing unit 800 dispensing from a stagger-folded or stacked array of gowns G.

While the invention has been described with reference to preferred and example embodiments, it will be understood by those skilled in the art that a variety of modifications, additions and deletions are within the scope of the invention, as defined by the following claims.

What is claimed is:

1. A dispenser for sleeved hospital gowns, comprising a frame, a receiver for receiving at least one sleeved hospital gown to be dispensed, the receiver comprising a cover for maintaining the sterility of the at least one sleeved hospital gown prior to dispensing, and a sensor to trigger a motor which rotates an internal cylinder containing an array of sleeved hospital gowns to dispense one of the sleeved hospital gowns from the receiver to a user, wherein the frame unfolds the dispensed gown and opens the sleeves for access to allow a user to place their arms in the sleeves and detach the gown from the dispenser without touching the dispenser or the outside of the gown.

2. The dispenser of claim 1, wherein the sensor is a touchless sensor.

3. An automated dispensing apparatus for gowns, the gowns having a body portion with sleeves extending therefrom, the apparatus comprising:
   an enclosure for storing a plurality of the gowns, each of the plurality of gowns having its body portion and sleeves folded compactly to form an array of compact gowns; and
   a dispensing mechanism for sequentially removing one of the plurality of gowns from the array of compact gowns within the enclosure and presenting them to a user outside of the enclosure, and unfolding the gown to allow access to the sleeves without contact between the dispensing apparatus and the user and without contaminating a clean portion of the gown being dispensed,
   wherein a dispenser arm descends with the gown during the removal or dispensing therefrom so as to push the gown away from the apparatus and toward the user, thereby creating a space for entry of the user's arms into the sleeves of the gown by the user.

* * * * *